(12) United States Patent
Shukla et al.

(10) Patent No.: US 7,560,120 B2
(45) Date of Patent: *Jul. 14, 2009

(54) VEHICLES FOR DELIVERY OF BIOLOGICALLY ACTIVE SUBSTANCES

(75) Inventors: Atul J. Shukla, Cordova, TN (US); James R. Johnson, Germantown, TN (US); Yichun Sun, Germantown, TN (US); Robert Cooper, Starkville, MS (US); Gregg Boring, Starkville, MS (US); Dan Scruggs, Starkville, MS (US)

(73) Assignee: University of Tennessee Research Foundation, Knoxville, TN (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/194,885

(22) Filed: Aug. 1, 2005

(65) Prior Publication Data

US 2005/0266083 A1 Dec. 1, 2005

Related U.S. Application Data

(63) Continuation of application No. 10/143,144, filed on May 9, 2002, now Pat. No. 6,960,346.

(51) Int. Cl.
*A61F 2/02* (2006.01)
(52) U.S. Cl. ..................................... 424/423
(58) Field of Classification Search ............. None
See application file for complete search history.

(56) References Cited

U.S. PATENT DOCUMENTS

| 4,297,353 | A | 10/1981 | Maulding |
| 5,047,166 | A | 9/1991 | Weil |
| 5,204,121 | A | 4/1993 | Bucheler |
| 5,352,662 | A | 10/1994 | Brooks |
| 5,591,727 | A | 1/1997 | Bencsits |
| 5,635,190 | A | 6/1997 | Cheetham |
| 5,747,058 | A | 5/1998 | Tipton |
| 5,958,937 | A | 9/1999 | Hausheer |
| 6,001,822 | A | 12/1999 | Wicks |
| 6,117,857 | A | 9/2000 | Carlsson |
| 6,673,767 | B1 * | 1/2004 | Brodbeck et al. .......... 514/2 |
| 6,960,346 | B2 * | 11/2005 | Shukla et al. ........... 424/400 |

OTHER PUBLICATIONS

"Dispersion", definition provided by Hawley's Condensed Chemical Dictionary, 14th Edition, 2002.*
"Suspension", definition provided by Hawley's Condensed Chemical Dictionary, 14th Edition, 2002.*
Morflex, Inc., Technical Bulletin 102, "Citrate Esters as Plasticizers for Aqueous Based Pharmaceutical Coatings" (1993).

(Continued)

*Primary Examiner*—Carlos A. Azpuru
(74) *Attorney, Agent, or Firm*—Howard Eisenberg, Esq.

(57) ABSTRACT

A formulation containing one or more biologically active substances dissolved, dispersed, emulsified, or suspended within a vehicle of one or more citric acid esters and/or citric acid ethers. Methods for making and using are disclosed, as are kits for administration of the pharmaceutical formulation.

14 Claims, 1 Drawing Sheet

OTHER PUBLICATIONS

Figure 1:
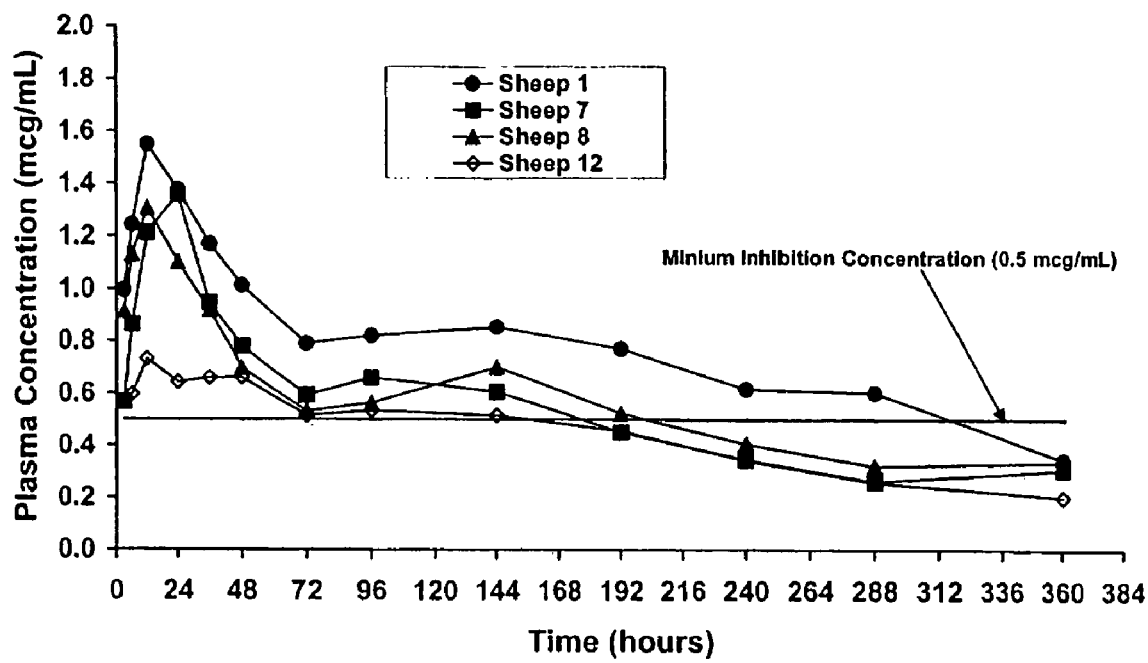

Morflex, Inc., Technical Bulletin 103, "Medical Grade Citroflex® Plasticizers" (1993).

Morflex, Inc., "Permanence of Plasticizers in Polymeric Films" (1993).

Morflex, Inc., Pharmaceutical Coatings Bulletin 102-1, "Influence of Citrate Ester Plasticizers on the Properties of Acrylic Resin Polymers" (1993).

Morflex, Inc., Pharmaceutical Coatings Bulletin 102-2, "Physical and Mechanical Properties of Acrylic and Cellulosic Polymers Plasticized with Citrate Esters" (1994).

Morflex, Inc., Pharmaceutical Coatings Bulletin 102-3, "Influence of Plasticizers on the Dissolution and Physical Properties of Ethyl Cellulose Films and Coated Beads" (1995).

Kennedy, SW, "Triethyl Citrate", in Kibbe, AH (ed.), Handbook of Pharmaceutical Excipients, 3rd ed., pp. 574-575, American Pharmaceutical Association (2000).

USP 23 NF 18 (United States Pharmacopoeia/National Formulary), "Pharmaceutical Dosage Forms", pp. 1944-1949 (1995).

Shah, NH, et al, "A Biodegradable Injectable Implant for Delivering Micro and Macromolecules using . . . ", Journal of Controlled Release, 27:139-147 (1993).

* cited by examiner

VEHICLES FOR DELIVERY OF BIOLOGICALLY ACTIVE SUBSTANCES

This application is a continuation of U.S. patent application Ser. No. 10/143,144 filed May 9, 2002 now U.S. Pat. No. 6,960,346.

FIELD OF THE INVENTION

The invention pertains to vehicles for delivery of biologically active substances. In particular, the invention pertains to compositions containing biologically active substances for administration to humans and animals or for application to the environment.

BACKGROUND OF THE INVENTION

Vehicles are essential components of formulations for administration of biologically active substances (BAS), such as drugs. The vehicle functions as a carrier for the BAS. The BAS is typically either dissolved dispersed, or suspended in the vehicle to form a solution, an emulsion, or a suspension. The physical form of a BAS-loaded vehicle may be a liquid, a gel, a semisolid, a paste, or a solid.

A BAS, and a vehicle containing a BAS, may be in any physical state for administration to a subject, such as by oral, topical, rectal, vaginal, or parenteral routes. Typically, for parenteral administration, solid forms of BAS must be rendered into a liquid or semisolid form, or suspended in a liquid vehicle, in order to be capable of being injected. Liquid forms of BAS also typically require a vehicle because the undiluted form of the BAS is generally too toxic to be administered directly. An undiluted BAS may irritate the site of injection. Diluting the BAS with a vehicle reduces the irritation. Also, diluting a BAS facilitates the administration of very small quantities of a BAS. These considerations are generally less important with application to the environment or with administration to a subject by other than parenteral routes. However, even with such non-parenteral administration, in many situations one or more of these considerations may be important.

The physiochemical properties of a vehicle are important in determining the release characteristics of the administered BAS. Typically pharmacological formulations containing a hydrophilic vehicle rapidly release their BAS into the body. In contrast, hydrophobic vehicles retard the contact of a BAS with aqueous body fluids and so can be used to control the release of a BAS from the site of administration. For many administration indications, such delayed release of a BAS from the site of administration is desired.

A vehicle should be pharmacologically inert, that is it does not produce a biochemical response by a body in which it is administered. The vehicle should also be non-irritating and non-toxic in the amounts administered. It should be stable and should not compromise the stability of the BAS.

An ideal vehicle has several additional characteristics. Ideally, a vehicle for parenteral use has good syringeability and injectability if the formulation is to be administered by a syringe. Ideally, the viscosity of a vehicle should be capable of being tailored so that a less viscous vehicle may injected as a liquid by a syringe, for example with parenteral administration, or may be applied by a spray, such as for topical or environmental applications. Conversely, a more viscous vehicle may be desirable to be smeared or applied in a gel or paste form, such as for topical administration or environmental application. Further, an ideal vehicle should be capable of being tailored to provide a range of hydrophilicity or hydrophobicity. Modification of viscosity and hydrophobicity or hydrophilicity of a vehicle permits a formulator to produce a composition having desired release characteristics, either an immediate or controlled release.

Water is the most commonly used vehicle for parenteral administration of BAS. However, it is unsuitable for controlled delivery of BAS because a drug dissolved in a water vehicle is immediately released into aqueous bodily fluids. Vehicles used for controlled delivery of BAS are typically fixed vegetable oils, polymer-based aqueous gels, and polymer-based water immiscible gels.

The following patents, each of which is incorporated herein by reference, disclose vehicles for controlled delivery of BAS. Maulding, U.S. Pat. No. 4,297,353, discloses a glyceride vehicle comprising a glycerol ester of a vegetable fatty acid. Carlsson, U.S. Pat. No. 6,117,857, discloses a vehicle of an admixture of a galactolipid extracted from plant material and a polar solvent, such as water, glycerol, ethanol, propylene glycol, polyethylene glycol, polypropylene glycol, glycofurol, methylpyrrolidone, or transcutol. Brooks, U.S. Pat. No. 5,352,662, discloses a vehicle for extended release formulations comprising a biocompatible hydrophobic vehicle such as sesame seed oil and a polyglycerol ester such as diglycerol tetrastearate. Tipton, U.S. Pat. No. 5,747,058, discloses a high viscosity liquid controlled delivery system in which the vehicle is a combination of sucrose acetate isobutyrate and a solvent which may be ethanol, dimethylsulfoxide, ethyl lactate, benzyl alcohol, triacetin, 2-pyrrolidone, N-methylpyrrolidone, propylene carbonate, or glycofurol. Wicks, U.S. Pat. No. 6,001,822, discloses an antiparasitic formulation in a vehicle of 50% to 95% sesame oil with the remainder ethyl oleate. Hausheer, U.S. Pat. No. 5,958,937, discloses a vehicle for producing a formulation of poorly water-soluble camptothecin and its analogues. The vehicle of Hausheer is N-methyl-2-pyrrolidinone with additives such as surfactant, polyethylene glycol, ethyl alcohol, and benzyl alcohol.

These and other prior art vehicles fail to provide the essential and ideal characteristics of a vehicle. The water based vehicles are not suitable for controlled release of a BAS. Like water based vehicles, aqueous gel vehicles are not suitable for sustained release of BAS, especially for very water-soluble BAS. The stability of a BAS is often compromised by the presence of fixed vegetable oils. A significant need exists for a vehicle that overcomes these and other disadvantages of currently available vehicles.

Esters of citric acid have been incorporated in a variety of compositions. Weil, U.S. Pat. No. 5,047,166, incorporated herein by reference, discloses several uses of salts of citric acid esters. The invention disclosed in Weil utilizes citric acid ester salts for their usefulness in providing a smooth and creamy feel to the skin. Weil further discloses that citric acid ester salts have been used in treating clothes, in food technology to retard rancidity and improve moisture retention, and have been employed as constituents of shampoos, deodorants, and soaps.

A major use of citric acid esters is as a plasticizer for polymers used as coatings for tablets and other oral forms of medication, such as capsules and caplets. The citric acid ester plasticizers are added to a solution or dispersion of a polymer and reduce the intermolecular attractions between polymeric chains. In so doing, the citrate ester increases the free volume of the polymer, allowing it to move more freely and so increase the polymer's workability, flexibility, and distensibility. Citric acid esters have also been used as plasticizers in film coatings, in toys for toddlers and infants, in plastic blood bags, and in plastic tubing used as catheters.

To date, there has been no disclosure of the use of citric acid esters as a vehicle for a BAS, such as in a pharmaceutical formulation or in a formulation for application to the environment.

SUMMARY OF THE INVENTION

It has been discovered that citric acid esters are ideal for use in a vehicle for the administration of a BAS. Citric acid esters are non-toxic and non-irritating, are pharmacologically inert, are physically and chemically stable, and do not compromise the stability of a BAS with which they are formulated. The viscosity of a citric acid ester vehicle may be tailored within wide ranges to provide, for example, a liquid, a semisolid, a solid, a gel, or a paste. Additionally, the hydrophilicity or hydrophobicity of these vehicles may be tailored to provide formulations that are useful for immediate release or delayed release indications, for example by combining different citrate esters or adding suitable additives.

A generic formula for citric acid esters that are suitable for the present invention is as follows.

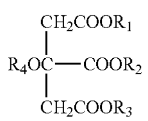

$R_1$, $R_2$, and $R_3$=H, saturated or unsaturated alkyl, cycloalkyl, or heterocyclic groups, or aryl groups $R_4$=H, saturated or unsaturated alkyl, cycloalkyl, or heterocyclic groups, or aryl groups, or RCO, where R=saturated or unsaturated alkyl, cycloalkyl, or heterocyclic groups, or aryl groups Also suitable for the present invention are citric acid ethers. These compounds are included in the above generic formula wherein $R_1$, $R_2$, and $R_3$ are H, and $R_4$ is an alkyl, cycloalkyl, heterocyclic, or aryl group. Because these citric acid ethers, like the esters, are suitable for the invention, the following description, which refers to citric acid esters, is applicable also to citric acid ethers or to combinations of citric acid esters and ethers. Thus, references below to a citric acid ester or to a CAE are intended to indicate a citric acid ester and/or a citric acid ether.

The various esters of citric acid vary in their hydrophilicity or hydrophobicity, and their water solubility. A citric acid ester may be used individually as a vehicle or it may be combined with one or more other citric acid esters to provide a custom vehicle having particular desired characteristics. Various additives may also be added to modify the physicochemical properties and release characteristics of a vehicle prepared with one or more citric acid esters. In this way, the hydrophobicity or hydrophilicity and/or the viscosity of a formulation may be modified. Also, the degree of solidity of a formulation may be modified by using a particular citric acid ester or combination of citric acid esters and/or by adding suitable additives.

In one embodiment, the invention is a formulation, such as a pharmacologic formulation, comprising one or more biologically active substances (BAS) and a citric acid ester vehicle. The formulation of the invention is preferably formulated so that the quantity of CAE in the formulation is sufficient to dissolve, disperse, emulsify, or suspend the entire amount of the BAS in the formulation. Most preferably, the formulation of the invention is formulated so that the entire amount of the BAS in the formulation is dissolved, dispersed, emulsified, or suspended in the citric acid ester vehicle. The formulation, as described more fully below, may be an immediate release formulation or a controlled release formulation. More than one citric acid ester may constitute the vehicle, which may provide for immediate release and/or controlled release. Additionally, the vehicle may contain one or more additives that can enhance or retard release of BAS, may alter viscosity, and may vary hydrophobicity or hydrophilicity of the vehicle and the formulation containing the vehicle and a BAS.

In another embodiment, the invention is a method for making a formulation, such as a pharmacologic formulation, which method comprises dissolving, dispersing, emulsifying, or suspending a BAS in a vehicle prepared with a citric acid ester. More than one BAS and/or more than one CAE may be used to make the formulation according to the method of the invention.

In another embodiment, the invention is a kit for treatment or prevention of a medical condition. According to this embodiment of the invention, the kit includes a packaging, at least one biologically active substance (BAS) within a container within the packaging, at least one citric acid ester (CAE) within a container within the packaging, and instructions within or on the packaging for applying the BAS and the CAE into the body or onto a body part of a patient, wherein the amount of BAS and CAE within the packaging are such that the amount of CAE is sufficient to dissolve, disperse, emulsify, or suspend the entire amount of the BAS, and preferably, when combined, the BAS is completely dissolved, dispersed, or suspended within the CAE.

In another embodiment, the invention is a method of treatment comprising administering to a patient in need thereof a pharmacologic formulation comprising one or more BAS and one or more CAE, wherein the entire amount of the BAS in the formulation is able to be dissolved, dispersed, emulsified, or suspended in the quantity of CAE in the formulation. According to this embodiment, such administration is preferably oral, parenteral, such as by injection or implantation, or may be by direct application to skin, a mucosal surface, or to a surface of a body cavity or an organ.

In another embodiment, the invention is a method for application of a BAS to the environment comprising administering to the environment a formulation comprising one or more BAS and one or more CAE, wherein the quantity of CAE in the formulation is sufficient to dissolve, disperse, emulsify, or suspend the BAS, and preferably the entire amount of the BAS in the formulation is dissolved, dispersed, emulsified, or suspended in the CAE.

BRIEF DESCRIPTION OF THE DRAWINGS

FIG. 1 is a graph showing the maintenance of plasma concentration of a BAS at or above the minimum inhibitory concentration for a prolonged period of time following a single injection of a BAS-loaded CAE.

FIG. 2 is a graph showing the release of a BAS from two formulations according to the invention (OTC in TEC or ATEC) compared to the release of the same BAS from a formulation of the prior art (OTC in PEG).

DETAILED DESCRIPTION OF THE INVENTION

Esters of citric acid (CAE) have been discovered to be ideally suited for vehicles for delivery of biologically active substances (BAS), such as pharmacologic agents, in a formulation, such as a pharmacological formulation. The use of such esters as a vehicle indicates that the amount of CAE in the formulation is sufficient to completely dissolve, disperse, emulsify, or suspend the BAS in the formulation. Preferably, BAS is completely dissolved, dispersed, or suspended in the CAE.

Virtually all CAEs, as defined above, are suitable as the vehicle of the invention. As a class, a CAE is non-toxic and non-irritating, pharmacologically inert, and physically and chemically stable, and does not compromise the stability of a BAS with which it is formulated. It is conceived that a particular CAE may prove to be unsuitable for a particular indication. However, in general, any CAE is suitable for use as a vehicle as described herein.

The CAE varies in its hydrophilicity or hydrophobicity. If desired, a combination of CAE may be utilized to prepare the vehicle, and such combination of CAE may include one or more CAE of differing hydrophilicity or hydrophobicity. Generally, a pharmaceutical formulation containing a hydrophilic vehicle will tend to release a BAS dissolved or suspended within the vehicle more rapidly than a similar formulation containing a hydrophobic vehicle. Additionally, a vehicle constituting a combination of hydrophilic and hydrophobic components may vary the release characteristics of the dissolved, dispersed, emulsified, or suspended BAS from the formulations.

The vehicle prepared with CAE may be in one of several physical states, depending upon the particular CAE, or combination of CAE, or types of additives incorporated in the formulation and the indication for which the formulation is to be used. For example, the vehicle prepared with CAE and the formulation may be a solid, a liquid, or a semisolid such as a paste, gel, ointment, or lotion. These and other types of pharmacological dosage forms are defined in USP 23 NF 18, pages 1944-1949 (1995), which is incorporated herein by reference.

The physiochemical properties and toxicity of several preferred CAE are indicated in Table 1.

most hydrophilic with a water solubility of 6.5% and a Log P value of 1.54. In contrast, B-6 is the most hydrophobic with a water solubility of less than 0.1% and a Log P value of 11.17.

Thus, the release characteristics and absorption of a BAS may be modulated by the hydrophilicity or hydrophobicity of the CAE used to prepare the vehicle, which may be further modified by combining two or more citric acid esters with varying hydrophilicity or hydrophobicity or by adding suitable additives. The release and absorption of a BAS may be further modified by modulating viscosity of the vehicle, such as by the addition of one or more additives. Additionally, the release of a BAS from the vehicle may be modulated by adding crystal growth inhibitors or complexing agents. Thus, controlled or immediate release of a BAS from the citric acid ester vehicle may be obtained by the use of a single ester as the vehicle or by combining one or more citrate esters, with additional modulation obtained by the use of appropriate additives.

Such additives may be used in combination with the citric acid ester in order to obtain certain desired properties of a formulation. Liquid, semisolid, or solid additives may be added, either singly or in combination, to the citric acid esters to modify the physicochemical as well as biological characteristics of the vehicle such as, hydrophilicity or hydrophobicity, consistency or viscosity, and absorption rate from injection, implantation, or application sites. Addition of hydrophilic liquid, semisolid or solid additives will increase the hydrophilicity of the citric acid ester vehicles, whereas, addition of hydrophobic liquid, semisolid or solid additives will increase the hydrophobicity of the citric acid ester vehicles. Hydrophilic vehicles may tend to degrade or be absorbed faster than the hydrophobic vehicles from the site of injection or application. Addition of semisolid and solid additives increases the viscosity of the vehicles, which generally decreases the release rate. It is possible to extend the in vivo duration of stay of the vehicle or delivery system by adding

TABLE 1

Physiochemical Properties and Toxicity of Several Preferred Citric Acid Esters*

|  | Triethyl Citrate (TEC) | Acetyl Triethyl Citrate (ATEC) | Tributyl Citrate (TBC) | Acetyl Tributyl Citrate (ATBC) | Acetyltri-n-hexyl Citrate (A-6) | Butyryltri-n-hexyl Citrate (B-6) |
|---|---|---|---|---|---|---|
| Molecular weight | 276.3 | 318.3 | 360.4 | 402.5 | 486 | 514 |
| Boiling Point (° C.) | 288 | 294 | 322 | 326 | N/A | N/A |
| Viscosity (cps) at 25° C. | 35 | 54 | 32 | 33 | 36 | 28 |
| Water Solubility at 25° C. (g/100 ml) | 6.5 | 0.72 | <0.1 | <0.1 | <0.1 | <0.1 |
| Log P Values** | 1.54 | 3.77 | 4.68 | 6.92 | 10.11 | 11.17 |
| Specific Gravity at 25° C. | 1.137 | 1.137 | 1.042 | 1.043 | 1.0046 | 0.991 |
| $LD_{50}$ | (Rat, SC) 6.6 g/Kg | (Rat, oral) 7.0 g/Kg | (Rat, oral) >30 g/Kg | (Rat, oral) >25 g/Kg | (Rat, oral) 20.0 g/Kg | (Rat, oral) 2.0 g/Kg |

*Data compiled from Technical Bulletins of various citric acid esters manufactured and distributed by Morflex, Inc., Greensboro, North Carolina
**Log P Values were calculated using ACD/Log P software (Advanced Chemistry Development, Inc., Ontario, Canada. Log P Values are indicative of the hydrophobicity of a material. Higher Log P Values indicate higher hydrophobicity.

As shown in Table 1, of the preferred citrate esters, TEC, ATEC, TBC, ATBC, A-6, and B-6 vary in their hydrophilicity or hydrophobicity, as shown by differences in water solubility and log P values. Of the CAEs shown in Table 1, TEC is the hydrophobic wax or other hydrophobic solid additives, which will increase both hydrophobicity and viscosity of the vehicle. The physical state of the CAE vehicle thus may be liquid, semisolid, solid, or a thick paste. The vehicle may be altered in this way to obtain a desired state depending on the intended use and the components of the vehicle and the formulation containing the vehicle.

Examples of liquid additives that are suitable to be combined with the citric acid ester vehicles of the invention as part of the formulations of the invention include, but are not limited to, water, water miscible or water immiscible solvents such as ethanol, ethyl lactate, phthalates such as dimethyl phthalate (DMP), diethyl phthalate (DEP), dibutyl phthalate (DBP), dioctyl phthalate, glycol ethers such as ethylene glycol diethyl ether, propylene glycol monomethyl ether, PPG-2 myristyl ether propionate, ethylene glycol monoethyl ether, diethylene glycol monoethyl ether, propylene glycol monotertiary butyl ether, dipropylene glycol monomethyl ether, N-methyl-2-pyrrolidone, 2 pyrrolidone, isopropyl myristate, isopropyl palmitate, octyl palmitate, dimethylacetamide, propylene glycol, propylene glycol monocaprylate, propylene glycol caprylate/caprate, propylene glycol monolaurate, glycerol, glycofurol, linoleic acid, linoeoyl macrogol-6 glycerides, oleic acid, oleic acid esters such as glyceryl dioleate, ethyl oleate, benzoic acid, oleoyl macrogol-6 glycerides, esters such as ethylbenzoate, benzylbenzoate, sucrose esters, sucrose acetate isobutyrate, esters of lactic acid, esters of oleic acid, sebacates such as dimethyl sebacate, diethyl sebacate, dibutyl sebacate, dipropylene glycol methyl ether acetate (DPM acetate), propylene carbonate, propylene glycol laurate, propylene glycol caprylate/caprate, gamma butyrolactone, polyethylene glycols (PEG), vegetable oils obtained from seeds, nuts, flowers, fruits, leaves, stem or any part of a plant or tree such as cotton seed oil, soy bean oil, almond oil, sunflower oil, peanut oil, sesame oil, corn oil, oils soluble vitamins such as vitamin A, D and E and K, vitamin E acetate, medium chain fatty acid triglycerides, glycerol and PEG esters of acids and fatty acids, PEG-6 glycerol mono oleate, PEG-6 glycerol linoleate, PEG-8 glycerol linoleate, caprylic acid esters such as caprylocapryl macrogol-8 glycerides, PEG-4 glyceryl caprylate/caprate, PEG-8 glyceryl caprylate/caprate, polyglyceryl-3-oleate, polyglyceryl-6-dioleate, polyglyceryl-3-isostearate, polyglyceryl polyoleate, decaglyceryl tetraoleate and glyceryl triacetate, glyceryl monooleate, glyceryl monolinoleate, dimethylformamide, dimethylsulfoxide, tetrahydrofuran, caprolactam, decylmethylsulfoxide, and, 1-dodecylazacycloheptan-2-one, surface active agents with varying hydrophilic lipophilic balance (HLB) values such as polyoxyethylene castor oil, polyoxyethylene hydrogenated castor oil, polyoxyethylene sorbitan fatty acid esters, polyoxyethylene alkyl esters, polyoxyethylene alkyl ethers, polyoxyethylene glycerol esters, sorbitan fatty acid esters, acetone, methyl acetate, ethyl acetate, methyl ethyl ketone, benzyl alcohol, acids such as hydrochloric acid, sulfuric acid, nitric acid, and phosphoric acid, citric acid, tartaric acid, and benzoic acid.

Examples of semisolid and solid additives that are suitable to be combined with the citric acid ester vehicles of the invention as part of the formulations of the invention include, but are not limited to, water soluble or insoluble solids such as polymers such as polyvinyl pyrrolidone, polyvinyl alcohol, ethylene vinyl acetate copolymer, cellulose derivatives, hydroxyethylcellulose, hydroxypropylcellulose, hydroxypropylmethylcellulose, methyl cellulose, sodium carboxymethylcellulose cellulose esters, cellulose acetate, cellulose propionate, cellulose acetate butyrate, waxes derived from animal, seeds, flowers, fruits, leaves, stem or any part of a plant or tree, hydrogenated oils, natural, semi-synthetic or synthetic waxes, carnauba wax, bees wax, aluminum salts, aluminum monostearate, magnesium hydroxide, aluminum hydroxide, paraffin, stearic acid, salts of stearic acid, cetyl alcohol, cholesterol, derivatives of beeswax and carnauba wax, saturated polyglycolized glycerides, semi-synthetic glycerides, glyceryl esters of fatty acids, glyceryl behenate, glyceryl di and tri stearate, glyceryl palmitostearate, lauroyl macrogol-32 glycerides, stearoyl macrogol-32 glycerides, polyethylene glycol esters of fatty acids such as PEG-32 glyceryl laurate, PEG-32 glyceryl palmitostearate, PEG-32 glyceryl stearate, cetyl palmitate, stearyl alcohol, cetyl alcohol, semisolid and solid surfactants, carbohydrates, sugars, sucrose, sorbitol, mannitol, zinc salts, tannic acid salts, salts of acids and bases such as sodium and potassium phosphates, sodium and potassium hydroxide, sodium and potassium carbonates and bicarbonates.

Virtually any BAS is suitable for the formulations of the invention containing one or more CAE as the vehicle for the BAS. The sole requirements for suitability of a BAS are that it be capable of being dissolved, dispersed (if the BAS is a liquid), suspended (if the BAS is a solid), or emulsified in the CAE and that it be physically and chemically compatible with the CAE vehicle.

The BAS that is dissolved, dispersed, emulsified, or suspended in the vehicle prepared with the CAE may in any physical state, such as a solid, a liquid, a semisolid, or a gas. Solid BAS may be crystalline or amorphous, or a combination thereof. Such solid BAS may be granulated with or without added excipients, and may be encapsulated in a material such as a polymer and/or a wax. A solid BAS may also be in the form of a matrix in which the BAS is distributed therein. A liquid BAS may be granulated, such as by absorption to a solid substrate, or encapsulated with a suitable solid, such as a polymer or wax or combination thereof.

Examples of BAS that are suitable for the invention include, but are not limited to, steroids such as corticosteroids, hormones, antipsychotic agents, agents that act on the central nervous system, narcotic agonists and antagonists, fertility regulating agents, antibodies and antigens, anesthetics, analgesics, antibiotics, antiviral agents, antineoplastic agents, antifungal agents, cavity and infection preventing agents, cardiovascular agents, angiogenic and antiangiogenic agents, anti-inflammatory agents, immunomodulators, vasodilators, bronchiodilators, alkaloids, peptides and proteins, vaccines, live or killed bacteria and viruses, agents or extracts derived from whole or parts of plants, trees, flowers, fruits, buds, seeds, leaves, barks, stem, roots, and animal tissues, growth promoting agents, soft and hard tissues, growth factors, human growth factor, human growth hormone, FGF, erythropoietin, granulocyte colony-stimulating factor (G-CSF), cells, tissues such as bones or agents derived therefrom, bone growth promoting agents such as calcium phosphates, calcium sulfate and hydroxyapatites, whole viable cells and cell-lines, genes, nucleic acid, antisense, deoxyribonucleic acid (DNA), DNA fragments, ribonucleic acid (RNA), RNA fragments, and biological tissues such as islets of langerhans and pancreas, insulin, vitamin and mineral supplements, iron, chelating agents, coagulants, and anticoagulants.

Particular BAS that are suitable for the invention include, but are not limited to, anticancer agents such as taxol, carmustine, interleukin 2, and interferon; growth hormones such as human growth hormone and somatotropin hormone; antipsychotic agents such as risperidone, and fluphenazine decanoate; antibiotics such as gentamicin, tetracycline, oxytetracycline, cephalosporins, aminoglycosides, and sulfonamides; oxytocic agents and prostaglandins; topical anesthetic agents such as benzocaine, chloroprocaine, cocaine, procaine, prbpoxycaine tetracaine, depravaine, bupivacaine, etidocaine, levobupivacaine, lidocaine, mepivacaine, prilocaine, propofol and ropivacaine; systemic analgesic agents such as morphine, oxycodone, fentanyl, sufentanyl, and butorphanol; narcotic antagonists such as naltrexone, nalorphine, naloxone, and nalmefene; growth promoting agents such as TGF alpha and TGF beta; bone morphogenic peptides and proteins and calcium salts such as calcium sulfate, calcium phosphate; anti-inflammatory agents such as diclofenac; steroids such as protaglandins, estrogens, androgens, and progestins; acne medications such as benzoyl peroxide; hair conditioners; sun screens; medications for skin conditions such as zinc oxide and those for treatment of psoriasis; ophthalmics such as lubricants and anti-glaucoma therapeutics; antibiotics such as quinolones; saliva substitutes; sedative/hypnotics such as benzodiazepines and barbiturates; wound care such as growth factors (EPO, FGF, G-CSF); antiparasitics for the treatment of diseases such as worms and malarial infestations; anticonvulsants; muscle relaxants; nucleoside analogs; osteoporosis preparations, such as to supplement bone growth; and antiparkinsonian agents.

The concentration of CAE in the vehicle prepared with one or more citric acid esters, in accordance with the formulation of the invention, is sufficient to completely dissolve, disperse, emulsify, or suspend the BAS. In most cases, the concentration of the vehicle in the formulations of the invention will be higher than that of any other component of the formulation. This is especially typical in the case of liquid formulations, such as formulations for topical administration such as ophthalmic or nasal drops, oral administration such as a soft or hard gel capsule, or formulations for administration by injection. Often, the concentration of the vehicle will be greater than 50% w/w of the formulation. The concentration of a BAS may be equal to or higher than that of the vehicle in a formulation, so long as the BAS is completely dissolved, dispersed, emulsified, or suspended in the vehicle. In particular cases, such as with certain liquid formulations containing a liquid drug dissolved or dispersed in a CAE, or a paste formulation containing a solid or semisolid BAS, the concentration of BAS may be higher than that of the vehicle. Notwithstanding, the BAS is completely dissolved, dispersed, emulsified, or suspended in the vehicle. In the case of semisolid or solid formulations, additives, such as waxes which are often added to obtain a desired viscosity, may be the major component of the formulation.

Solid or semisolid formulations of the invention, such as emulsions or solutions in the form of ointments, creams, lotions, and gels, typically contain additional components other than a BAS and the CAE. In these formulations, as in liquid formulations, the CAE is often the major component. However, if desired, the CAE in the formulation may be a minor component, that is the concentration of the CAE may be lower than one or more other constituents of the formulation. For example, the concentration of the CAE may be as low as 3% w/w or even lower. Higher CAE concentrations, such as 10%, 25%, 50% or more are also conceived.

In a preferred embodiment, a pharmacologic formulation for topical administration, such as for administration to skin or to a mucosal surface, includes a vehicle of one or more CAE, a BAS that is completely dissolved, suspended, emulsified, or dispersed in the vehicle. The formulation may include a gelling agent, such as a stearate compound like aluminum monostearate. Other ingredients, such as preservatives, humectants, and chelating agents, may also be included in the formulation as desired.

If desired, compounds that are typically used as vehicles may be included with the CAE in the formulation. Thus, the formulation may contain, for example, water, a glycol, an oil phase or other compound used as a vehicle in formulations. Where one or more of these additional vehicles is included in the formulation, the concentration of the CAE in the formulation is either sufficient to dissolve, disperse, emulsify, or suspend the entire quantity of the BAS in the formulation, in the absence of the additional vehicle, and/or is higher than that of any other single vehicle in the formulation.

The composition of the invention containing one or more BAS and one or more CAE may be made by any method wherein the quantity of CAE is sufficient to dissolve, disperse, emulsify, or suspend the entire quantity of the BAS in the composition. Preferably, the entire quantity of the BAS is dissolved, dispersed, emulsified or suspended in the CAE. Typically, the BAS and CAE are combined, such as by blending or mixing until the BAS is completely dissolved, or uniformly dispersed, emulsified, or suspended in the CAE. Additives, such as those described above, may be combined with the BAS and the CAE before, after, or during the combining of the BAS and the CAE.

In one preferred embodiment, the BAS and the vehicle prepared with CAE are maintained in separate containers during storage and are combined with each other to obtain a formulation prior to use of the formulation. The separate storage of BAS and CAE vehicle has several advantages which may or may not be important for particular indications. For example, separate storage of BAS and CAE vehicle permits the prolonged storage of BAS in situations where a BAS would tend to degrade following combination. This may occur, for example, with vaccines that are stored in a freeze-dried condition and only combined with a vehicle just prior to inoculation. Separate storage of BAS and CAE vehicle further permits the tailoring of the dose of the BAS by permitting the combination of a particular requisite amount of the BAS into a quantity of vehicle prepared with CAE to be administered. Separate storage of BAS and CAE also permits either or both of the BAS and CAE to be treated in ways which would be harmful to the other component. For example, the CAE may be sterilized by gamma-irradiation, which might not be appropriate for certain BAS.

The kit of the invention contains one or more BAS and a vehicle prepared with one or more CAE, which BAS and vehicle are housed in one or more containers within a packaging. The vehicle and/or the BAS may be combined with one or more suitable additives. The amounts of BAS and CAE vehicle in the kit are such that, when contained in one container, the quantity of CAE in the container is sufficient to completely dissolve, disperse, emulsify, or suspend the BAS. Preferably, the entire quantity of the BAS is completely dissolved, dispersed, emulsified, or suspended within the CAE vehicle. The kit preferably contains written instructions on or within the packaging that state how the BAS that is dissolved, dispersed, emulsified, or suspended within the CAE vehicle is to be administered into or onto a body part of a patient. The kit may contain the BAS and the CAE vehicle housed within a single container. Alternatively, the BAS and the CAE vehicle may be stored in separate containers within the kit. In this case, preferably the instructions further state how the BAS and CAE vehicle are to be combined before administration.

According to the method of treatment embodiment of the invention, a medical condition is sought to be prevented or treated by administering to a patient a pharmaceutical composition, as described above, comprising a BAS and a CAE wherein the quantity of CAE in the composition is sufficient to completely dissolve, disperse, emulsify, or suspend the BAS. Preferably, the BAS is completely dissolved, dispersed, emulsified, or suspended within the CAE vehicle. The administration may be internal, such as oral or parenteral, such internal parenteral administration including but not limited to intravascular, intramuscular, subcutaneous, intradermal, intrathecal, and intracavitary routes of administration, as well as application to the external surface of an internal bodily organ, such as during a surgical or laparoscopic procedure. The administration may be topical, including administration to the skin or to a mucosal surface, including the oral, vaginal, rectal surfaces, to the surface of the eye, to the nasal passages, or to the ear canal.

According to the method of application embodiment of the invention, a formulation containing a BAS and a CAE vehicle, in which formulation the quantity of CAE is sufficient to dissolve, disperse, emulsify, or suspend the entire quantity of the BAS in the formulation, and preferably in which formulation the entire quantity of BAS is dissolved, dispersed, or emulsified, or suspended within the CAE vehicle, is applied to the environment. The formulation may be in the form of a solid, a semisolid, or a liquid. The means of application to the environment is immaterial and will depend on the particular environmental substrate that is being treated and the BAS that is being applied. For example, the formulation may be applied to bodies of water, such as rivers, lakes, or oceans, to the atmosphere, or to land. It is evident that the physical state of the formulation and the particular method of application may vary accordingly.

The invention is further described in the following illustrative, non-limiting, examples.

EXAMPLE 1

A pharmaceutical formulation containing 20% oxytetracycline (OTC) suspended in a vehicle of acetyl triethyl citrate (ATEC) was injected subcutaneously into 4 adult sheep. The minimum inhibitory concentration of OTC has been previously determined to be 0.5 mcg/ml. Blood samples were obtained from each of the four sheep at 3, 6, 12, 24, 36, 48 hours day 3, day 4, day 6, day 8 day 10, and day 15 after subcutaneous injection. Plasma concentrations of OTC were determined by an HPLC method.

As shown in FIG. 1, following the single injection of OTC in ATEC, the plasma concentration of OTC in each sheep peaked at about 12 hours following injection and then declined. The plasma concentration of OTC in each of the four sheep remained above the minimum inhibitory concentration for at least 6 days in each of the sheep, and in two of the four sheep remained above the minimum inhibitory concentration for 192 hours (8 days). In one of the sheep, the plasma concentration of OTC in ATEC remained above the minimum inhibitory concentration at 288 hours (12 days).

EXAMPLE 2

Figure 2:
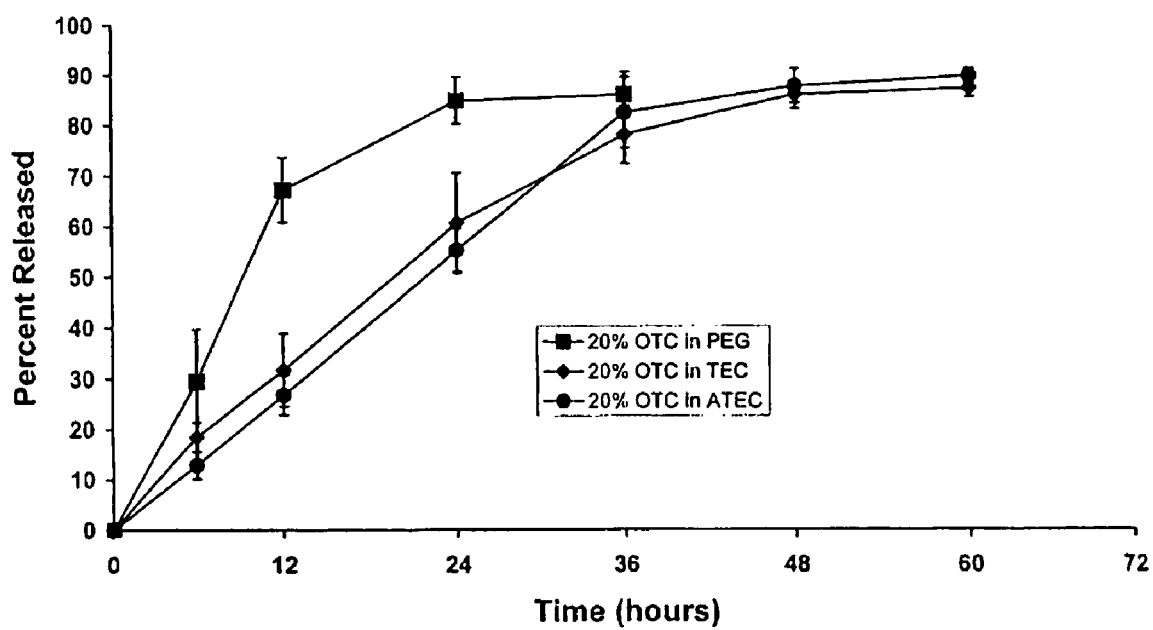

Appropriate quantities of oxytetracycline (OTC) were blended with either polyethylene glycol (PEG), triethyl citrate (TEC), or acetyl triethyl citrate (ATEC) to yield formulations with 20% OTC. The release of OTC from these formulations was evaluated in pH 7.4 phosphate buffer at 37° C. The cumulative percentage of OTC released from the formulations was determined at 6 and 12 hours, and each 12 hours thereafter until 60 hours (2.5 days). As shown in FIG. 2, release of OTC from the PEG vehicle was more rapid at all time points up to 36 hours. At 12 hours, almost 70% of the OTC had been released by the PEG vehicle, whereas about 30% or less had been released from each of the two citrate vehicles.

This Example illustrates how the release characteristics of a BAS may be altered by using vehicles that differ in their hydrophilicity. PEG 400 (Log P value of −1.44) is more hydrophilic than TEC (Log P value of 1.54) and ATEC (Log P value of 3.77). PEG 400 is also freely miscible with water. TEC and ATEC are less water soluble than is PEG. The water solubility of TEC is 6.7% and that of ATEC is less than 1%.

All articles and patents cited in this application are incorporated herein by reference.

Further modifications, uses, and applications of the invention described herein will be apparent to those skilled in the art. It is intended that such modifications be encompassed in the following claims.

The invention claimed is:

1. A composition comprising a biologically active substance (BAS) and a citric acid ester (CAE) and/or a citric acid ether, wherein the amount of the CAE and/or the ether in the composition is sufficient to dissolve, disperse, emulsify, or suspend the entire amount of the BAS in the composition, and the BAS in the composition is dissolved, dispersed, emulsified, or suspended in the citric acid ester or ether wherein the CAE and/or the citric acid ether is present in the composition in a concentration higher than that of any other constituent of the composition.

2. The composition of claim 1 wherein the CAE is selected from the group consisting of triethyl citrate, acetyl triethyl citrate, tri-n-butyl citrate, acetyl tri-n-butyl citrate, acetyl tri-n-hexyl citrate, and butyryl tri-n-hexyl citrate.

3. The composition of claim 1 wherein the composition comprises a multiplicity of different CAEs and/or citric acid ethers.

4. The composition of claim 1 which frrther contains a polymer,

5. The composition of claim 1 wherein the concentration of the CAE and the citric acid ether in the composition is greater than 3% w/w.

6. The composition of claim 5 wherein the concentration of the CAE and the citric acid ether in the composition is greater than 10% w/w.

7. The composition of claim 6 wherein the concentration of the CAE and the citric acid ether in the composition is greater than 25% w/w.

8. The composition of claim 7 wherein the concentration of the CAE and the citric acid ether in the composition is greater than 50% w/w.

9. The composition of claim 1 which further contains a gelling agent

10. The composition of claim 1 which is a liquid.

11. The composition of claim 1 which is a semi-solid, a gel, a paste, or a solid.

12. The composition of claim 1 wherein the CAE or citric acid ether is hydrophobic.

13. The composition of claim 1 wherein the CAE or citric acid ether is hydrophilic.

14. The composition of claim 1 which further comprises a wax.

* * * * *